(12) United States Patent
Hematti et al.

(10) Patent No.: US 9,994,819 B2
(45) Date of Patent: Jun. 12, 2018

(54) XENO-FREE GENERATION OF TISSUE-SPECIFIC PROGENITOR CELLS

(71) Applicant: WISCONSIN ALUMNI RESEARCH FOUNDATION, Madison, WI (US)

(72) Inventors: Peiman Hematti, Middleton, WI (US); Jaehyup Kim, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 78 days.

(21) Appl. No.: 15/154,653

(22) Filed: May 13, 2016

(65) Prior Publication Data
US 2016/0257933 A1 Sep. 8, 2016

Related U.S. Application Data

(63) Continuation of application No. 13/231,753, filed on Sep. 13, 2011, now Pat. No. 9,359,593.

(60) Provisional application No. 61/382,095, filed on Sep. 13, 2010.

(51) Int. Cl.
| | |
|---|---|
| *C12N 5/09* | (2010.01) |
| *C12N 5/0789* | (2010.01) |
| *G01N 33/50* | (2006.01) |
| *A61K 35/28* | (2015.01) |
| *C12N 5/071* | (2010.01) |
| *A61K 35/12* | (2015.01) |

(52) U.S. Cl.
CPC .......... *C12N 5/0647* (2013.01); *A61K 35/28* (2013.01); *C12N 5/0676* (2013.01); *C12N 5/0693* (2013.01); *C12N 5/0694* (2013.01); *G01N 33/5073* (2013.01); *A61K 2035/124* (2013.01); *C12N 2502/1157* (2013.01); *C12N 2502/1358* (2013.01); *C12N 2506/02* (2013.01); *C12N 2506/22* (2013.01)

(58) Field of Classification Search
None
See application file for complete search history.

(56) References Cited

PUBLICATIONS

Bessis et al., "Iron metabolism in the bone marrow as seen by electron microscopy: a critical review." Blood 19:635-663 (1962).
Chasis et al., "Erythroblastic islands: niches for erythropoiesis." Blood. 112:470-478 (2008).
Cheng et al., "Human adult marrow cells support prolonged expansion of human embryonic stem cells in culture." Stem Cells 21:131 (2003).
Dominici et al., "Minimal criteria for defining multipotent mesenchymal stromal cells. The International Society for Cellular Therapy position statement." Cytotherapy 8(4):315 (2006).
Dorrell, "Isolation of major pancreatic cell types and long-term culture-initiating cells using novel human surface markers." Stem Cell Res. 1(3):183-194 (2008).
Eisenberg, et al. "Stem Cell Plasticity, Cell Fusion, and Transdifferentiation" Birth Defects Research, 69, 209-218, 2002.
Gordon, "The macrophage: past, present and future." Eur J Immunol. Nov. 2007; 37 Suppl 1:S9-17.
Hideshima et al., "Understanding multiple myeloma pathogenesis in the bone marrow to identify new therapeutic targets." Nat. Rev. Cancer 7:585-598 (2007).
Honda, et al., "In-vitro enhancement of mouse embryonic development by co-culture with peritonel macrophages" Human Reproduction, 9, 692-696, 1994.
Jaiswal et al., "CD47 is upregulated on circulating hematopoietic stem cells and leukemia cells to avoid phagocytosis." Cell 138:271 (2009).
Kaufman et al., "Hematopoietic colony-forming cells derived from human embryonic stem cells" PNAS 98(19):10716 (2001).
Khazen, et al. "Expression of macrophage-selective markers in human and rodent adipocytes" Federation of European Biochemical Societies, 579, 5631-5634, 2005.
Ludwig et al. "Feeder-independent culture of human embryonic stem cells." Nat. Methods 3(8):637-646 (2006).
Nakano et al., "Generation of lymphohematopoietic cells from embryonic stem cells in culture" Science 265(5175):1098 (1994).
Narayan et al., "Human embryonic stem cell-derived hematopoietic cells are capable of engrafting primary as well as secondary fetal sheep recipients." Blood 107:2180 (2005).
Parenteau "Commercial development of cell-based therapeutics: strategic considerations along the drug to tissue spectrum" Regenerative Medicine, vol. 4, No. 4, pp. 601-611 (2009).
Pollard, "Trophic macrophages in development and disease." Nature Rev. 9:259-270 (2009).
Simon et al., "The role of oxygen availability in embryonic development and stem cell function" Nat. Rev. Mol. Cell Biol. 9(4):285 (2008).
Stella et al., "CD34-Positive Cells: Biology and Clinical Relevance" Haematologica 80(4):367 (1995).
Stout et al., "Macrophages sequentially change their functional phenotype in response to changes in microenvironmental influences" J. Immunol. 175:342-349 (2005).
Tarnok et al., "Phenotypes of stem cells from diverse origin." Cytometry 77(1):6-10 (2010).
Trivedi, et al. "Derivation and immunological characterization of mesenchymal stromal cells from human embryonic stem cells" Exp. Hematol. 36(3):350-359 (2008).
Trivedi, et al., "Simultaneous generation of CD34+ primitive hematopoietic cells and CD73+ mesenchymal stem cells from human embryonic stem cells cocultured with murine OP9 stromal cells" Experimental Hematology, 35, 146-154, 2007.
Urbaniak Hunter et al., "Gene- and cell-based approaches for neurodegenerative disease." Adv. Exp. Med. Biol. 671:117-130 (2010).
Vodyanik et al., "Human embryonic stem cell-derived CD34+ cells: efficient production in the coculture with OP9 stromal cells and analysis of lymphohematopoietic potential" Blood 105(2):617(2005).

(Continued)

*Primary Examiner* — David W Berke-Schlessel
(74) *Attorney, Agent, or Firm* — Quarles & Brady LLP

(57) ABSTRACT

The invention relates to purified, tissue-specific progenitors, methods of making and using such tissue-specific progenitors.

9 Claims, 9 Drawing Sheets

(56) References Cited

PUBLICATIONS

Yang et al., "CD3(+) and/or CD14(+) depletion from cord blood mononuclear cells before ex vivo expansion culture improves total nucleated cell and CD34(+) cell yields." Bone Marrow Transplant. 45(6):1000 (2010).

Zheng et al., "Macrophages are an abundant component of myeloma microenvironment and protect myeloma cells from chemotherapy drug-induced apoptosis" Blood. Oct. 22, 2009;114(17):3625-8.

Kim et al., "Mesenchymal stem cell-educated macrophages: a novel type of alternatively activated macrophages" Exp Hematol. 2009; 37(12):1445-1453.

Doetschman et al., "The in vitro development of blastocyst-derived embryonic stem cell lines: formation of visceral yolk sac, blood islands and myocardium" (1985) J. Embryol. Exp. Morphol. 87, 27-45.

FIG. 2A 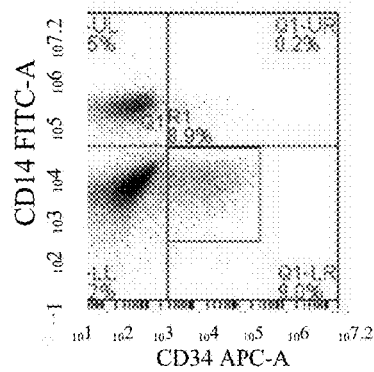 FIG. 2B 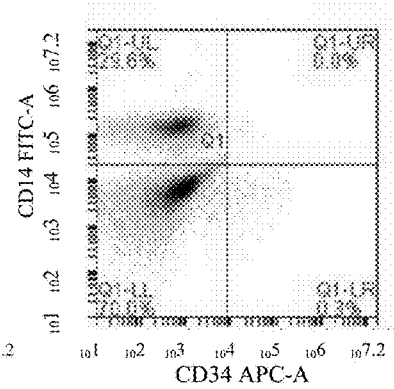
FIG. 2C 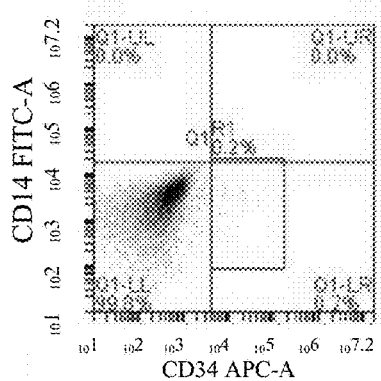 FIG. 2D

CONTROL          Wnt pathway Agonist

XENO-FREE GENERATION OF TISSUE-SPECIFIC PROGENITOR CELLS

CROSS-REFERENCE TO RELATED APPLICATION

This application is a continuation application of U.S. application Ser. No. 13/231,753, filed Sep. 13, 2011, which claims the benefit of U.S. Provisional Patent Application No. 61/382,095, filed Sep. 13, 2010, each of which is incorporated herein by reference as if set forth in its entirety.

STATEMENT REGARDING FEDERALLY SPONSORED RESEARCH OR DEVELOPMENT

This invention was made with government support under HL081076 awarded by the National Institutes of Health. The government has certain rights in the invention.

BACKGROUND

Tissue-specific progenitor cells, also known as tissue-specific or adult stem cells, are rare populations of cells present in many adult tissues capable of differentiating into various cells specific to the tissue in which they reside. For example, hematopoietic stem cells (HSCs) are a rare population of cells inside the bone marrow that are responsible for generating all types of blood cells. Similar tissue-specific progenitor cells reside in other tissues, such as brain, heart, liver, and pancreas and can give rise to cells of their respective tissues. These cells hold great promise for clinical use to regenerate damaged or lost tissue. Clinical use has been hampered, in part, by an inability to isolate or produce sufficient numbers of tissue-specific progenitor cells suitable for clinical application. At present, HSCs are the only adult stem cells in clinical use, but their use is restricted by the limited availability of these cells. There is, thus, a need in the art for methods of producing tissue-specific progenitor cells in vitro that are suitable for clinical application.

Hematopoietic stem cells (HSCs) are the best-characterized example of tissue-specific progenitor cells. Successful engraftment of a small number of $CD34^+$ HSCs can sustain hematopoiesis for a lifetime. The study of human hematopoiesis has been greatly advanced by the development of methods to generate HSCs from human embryonic stem cells (hESCs) (Kaufman et al., PNAS 98(19):10716 (2001); Vodyanik et al., Blood 105(2):617(2005)). Effective methods of generating tissue-specific progenitor cells suitable for clinical use, such as HSCs, from hESCs could provide a novel source of progenitors for transplantation. In addition, hESC-derived tissue-specific progenitor cells can be used to produce various tissue cells that can be used for clinical and pharmaceutical research or can be administered to individuals in need thereof.

Unfortunately, currently available methods include culturing hESCs on murine bone marrow stromal cells, which is undesirable for preparing cells intended for clinical use (Nakano et al., Science 265(5175):1098 (1994)). Within the body, HSCs are maintained in an undifferentiated state within bone marrow microenvironments or "niches." These HSC niches are thought to regulate survival, self-renewal, and maintenance of HSCs through growth factor and cytokine secretion, structural support, and direct cell-to-cell crosstalk. The cellular microenvironment is comprised of various cell types in the bone marrow stromal including mesenchymal stem cells (MSCs), vascular endothelial cells, and reticular cells.

Mesenchymal stem cells (MSCs) are fibroblast-like cells that reside within virtually all tissues and organs of a postnatal individual and can differentiate into cells of the mesenchymal lineage, such as osteoblasts, adipocytes, and chondrocytes. MSCs have been isolated from bone marrow, adipose tissue, heart, pancreas, liver, kidney, and other tissues. Tarnok et al., Cytometry 77(1):6-10 (2010). Within the bone marrow niche, MSCs support survival, proliferation, and differentiation of HSCs and their progeny through a variety of mechanisms, such as by producing extracellular matrix components for structural support and by secreting growth factors and cytokines that support HSC maintenance and proliferation. Long-term bone marrow cultures demonstrated the importance of MSCs in hematopoietic stem and progenitor cell maintenance ex vivo and MSCs have provided invaluable tools for investigating the stem cell niche in both normal and malignant hematopoiesis. Human MSCs can support hESC expansion in vitro (Cheng et al., Stem Cells 21:131 (2003)).

Apart from MSCs, a wide variety of other cell types contribute to normal bone marrow function. For example, osteoblasts, which are differentiated progeny of MSCs, are critical in HSC niche maintenance while adipocytes, also differentiated progeny of MSCs, are negative regulators of hematopoiesis.

Macrophages are present in almost all tissues and are essential to innate immunity. Like other hematopoietic cells, macrophages originate from a bone marrow progenitor cell that first gives rise to monocytes. Monocytes circulate in the peripheral blood and can give rise to macrophages after extravasating from the blood stream into the surrounding tissue, either to replace long-lived tissue macrophages or in response to injury. Gordon, European J Immunol. 37 Suppl 1:S9-17 (2007). Within the tissue, macrophages can be polarized by their microenvironment to assume different phenotypes. Stout et al., J. Immunol. 175:342-349 (2005). For example, certain macrophages are essential for all stages of tissue repair including chemotaxis, matrix remodeling, epithelial migration, and angiogenesis (Pollard, Nature Rev. 9:259-270 (2009)).

The data on macrophage involvement in hematopoiesis are conflicting. Macrophages have been implicated in erythropoiesis. Transmission electron micrographs showed erythroblasts surrounding a central macrophage. Bessis and Breton-Gorius, Blood 19:635-663 (1962). These "erythroblastic islands" play a crucial role in normal erythroid development by providing iron for heme synthesis and erythropoietin for erythropoiesis to developing erythroblasts. Abnormal erythroblastic islands are associated with altered erythropoiesis of pathological processes such as anemia of inflammation and chronic disease, myelodysplasia, and thalassemias. Chasis et al., Blood. 112:470-478 (2008). In all these conditions, the role of macrophages has been assumed to be restricted to erythropoiesis.

In contrast, recent studies suggest that monocytes and macrophages negatively affect in vitro expansion of HSC and hematopoiesis (Yang et al., Bone Marrow Transplant. 45(6):1000 (2010); Jaiswal et al., Cell 138:271 (2009)). A recent study suggests that HSCs respond to inflammatory stimuli and upregulate CD47, which then interacts with macrophage receptors to evade macrophage-mediated destruction among the toxic inflammatory milieu. Thus, the role of macrophages as a direct-acting component of the HSC niche was unknown prior to the inventors' work. Further, it was not known whether MSCs and macrophages interact and whether such interactions affect survival and proliferation of HSCs.

While HSCs have been studied extensively, little is known about tissue-specific progenitor cells of other tissues. Until recently, it was believed that the heart and brain contained only terminally differentiated cells unable to proliferate. However, recent studies identified a subpopulation of cells in the heart, brain, and other organs that are able to proliferate and repopulate damaged or destroyed tissues. There is a great need in the art for methods for enhancing proliferation of these cells in vivo or in vitro.

Interactions between macrophages and tumor cells in hematological malignancies, with the exception of follicular lymphoma, are not well understood. Recent studies suggest that macrophages can promote angiogenesis in multiple myeloma (MM), the second most commonly diagnosed hematological malignancy in the developed world. Also, macrophages might protect myeloma cells from spontaneous and chemotherapy-induced apoptosis. Zheng et al., Blood 22;114(17):3625-3628 (2009). However, the role of BM macrophages as a direct-acting component in the MM tumor niche has not been recognized. Further, it has not been investigated if MSCs-macrophage interaction affects survival and proliferation of MM cells. The multitude of cellular compartments and the broad constellation of growth factors and cytokines involved in the MM tumor niche pose significant therapeutic challenges. Targeting any individual molecular or cell mediator of the MM BM milieu is not sufficient for curative responses due to functional redundancy supporting MM cell survival. New models to investigate the functional hierarchy of the BM microenvironment are necessary to devise effective therapeutic strategies.

Prior to the inventors' work, it was unknown whether cellular interaction of MSCs with another cell type can affect function of a third cell type. Prior to the inventors' work, it was further unknown whether the origin of the MSC affects the quality of interaction with, and subsequent fate of, another cell.

BRIEF SUMMARY

The present invention is broadly summarized as relating to methods for generating tissue-specific progenitor cells from pluripotent cells. While progenitors have been generated in culture, they required culture with cells from different species, e.g., human pluripotent cells on murine feeder cells. The inventors developed novel methods that employ cells of only one species.

In a first aspect, the invention is summarized in that a method for producing a tissue-specific progenitor includes the step of co-culturing a $CD14^+$ cell, a tissue-specific MSC, and a pluripotent cell in vitro to produce the tissue-specific progenitor cell. In some embodiments of the first aspect, all three cells are from the same species. In some embodiments of the first aspect, the method is conducted under completely xeno-free conditions.

In a second aspect, the invention relates to a population of tissue-specific progenitor cells generated by co-culturing a $CD14^+$ cell, a tissue-specific MSC, and a pluripotent cell in vitro to produce a tissue-specific progenitor cell. In some embodiments of the second aspect, the tissue-specific progenitor cells express CD26.

In a third aspect, the invention relates to a cell culture composition comprising a $CD14^+$ cell, a tissue-specific MSC, and a pluripotent cell. Some or all of the cells of the cell culture composition can be allogeneic with regard to each other. Likewise, some or all of the cells of the cell culture composition can be syngeneic or autologous to each other.

In a fourth aspect, the invention relates to a cell culture composition comprising a $CD14^+$ cell, a tissue-specific MSC, a pluripotent cell, and a tissue-specific progenitor cell. The composition can optionally further comprise a compound of interest to investigate the compound's effect on the culture composition.

In a fifth aspect, the invention relates to methods for treating a disorder associated with aberrant loss of normal cell function comprising the step of administering to an individual in need thereof a tissue-specific progenitor cell. The progenitor cell used in these methods can be allogeneic, syngeneic, or autologous with regard to the individual.

In a sixth aspect, the invention relates to methods for in vitro testing of compounds by co-culturing a $CD14^+$ cell, a tissue-specific MSC, and a pluripotent cell in vitro to produce the tissue-specific progenitor cell and then contacting the progenitor cell with the compound of interest. The progenitor cell can be cultured either under conditions that promote or prevent differentiation, depending on whether the compound is to be tested for its effect on undifferentiated progenitors or the differentiation process. Alternatively, the compound of interest can be added to the $CD14^+$ cell, tissue-specific MSC, and pluripotent cell culture composition prior to production of the tissue-specific progenitor cell.

In a seventh aspect, the invention relates to methods for culturing a malignant cell in vitro by co-culturing a malignant cell with a $CD14^+$ cell such that the malignant cell proliferates. The $CD14^+$ cell can be an MSC-educated macrophage. As used herein, "MSC-educated macrophage" refers to a macrophage that was generated by co-culturing a $CD14^+$ cell with an MSC. Optionally, an MSC can be added to the malignant cell-$CD14^+$ cell co-culture. The malignant cell, such as a myeloma cell, can be isolated from a human individual.

In an eighth aspect, the invention relates to methods for culturing a $CD34^+$ cell in vitro by co-culturing a $CD34^+$ cell with a $CD14^+$ cell in vitro such that the $CD34^+$ cell proliferates. The $CD14^+$ cell can be an MSC-educated macrophage. Optionally, the $CD34^+$ cell is co-cultured with a $CD14^+$ cell and an MSC.

Unless otherwise defined, all technical and scientific terms used herein have the same meaning as commonly understood by one of ordinary skill in the art to which this invention belongs. Although suitable materials and methods for the practice or testing of the present invention are described below, other materials and methods similar or equivalent to those described herein, which are well known in the art, can be used.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE SEVERAL VIEWS OF THE DRAWINGS

The present invention will be better understood and features, aspects and advantages other than those set forth above will become apparent when consideration is given to the following detailed description thereof. Such detailed description makes reference to the following drawings, wherein:

FIG. 2A-D illustrate results of flow cytometric analysis. FIG. 2A shows that co-cultures of ESC, bone marrow-derived MSC, and CD14$^+$ cells produce CD34$^+$ cells. FIG. 2B shows that co-cultures of ESC, pancreatic islet-derived MSC, and CD14$^+$ cells produce very few CD34$^+$ cells. ESC and CD14$^+$ cells used were the same as in FIG. 2A. FIG. 2C shows that ESC-MSC co-cultures without CD14$^+$ cells did not lead to generation of CD34$^+$ cells. FIG. 2D shows that the addition of CD14$^+$ cells to ESC-MSC co-cultures results in generation of CD34$^+$ cells. The same ESCs and bone marrow MSCs were used for FIGS. 2C and 2D.

DETAILED DESCRIPTION OF PREFERRED EMBODIMENTS

The present invention broadly relates to methods for generation of tissue-specific progenitor cells from pluripotent cells. These progenitor cells can be generated by co-culturing tissue-specific MSCs with pluripotent cells and CD14$^+$ cells. The novel method is useful for producing adult stem cells/progenitors of desired tissue lineages for research and clinical application. Advantageously, the novel method can be conducted under xeno-free conditions.

As used herein, "xeno-free" or "xeno-free conditions" refers to cellular co-culture using only cells from a single species, i.e., the cells of the co-culture are allogeneic, syngeneic, or autologous with respect to each other.

As used herein, "monocyte" refers to a mononuclear leukocyte that can differentiate into a macrophage.

As used herein, "macrophage" refers to a mononuclear phagocyte characterized by the expression of CD14 and lack of expression of dendritic cell markers.

As used herein, "CD14$^+$ cell" refers to a monocyte or a macrophage.

CD14$^-$ cells and pluripotent cells used for co-culture can be obtained from any suitable source. The skilled artisan will appreciate the advantageous efficiency of generating macrophages from peripheral blood monocytes for co-cultures. Alternatively, macrophages can also be isolated from individuals directly, such as through cellular outgrowth from tissue samples. Likewise, the skilled artisan will appreciate the advantageous efficiency of using induced pluripotent stem cells, especially those from autologous somatic cells, as pluripotent cells. Alternatively, pluripotent cells can be obtained from various sources, such as commercially available stem cell lines.

Likewise, MSCs used for co-culture can be obtained from any suitable source. The source of the MSC directs differentiation of the pluripotent cells in co-culture. For example, MSCs from bone marrow direct pluripotent cell differentiation towards the hematopoietic lineage. MSCs from the heart direct pluripotent cell differentiation towards the cardiac lineage.

As such, selecting a source of the MSC can depend upon the desired culture objective. For example, if the culture objective is to generate a hematopoietic stem cell, then MSCs from bone marrow are appropriate. Likewise, if the desired progenitor cell is a cardiomyocyte progenitor cell, then heart tissue can be an appropriate choice for MSCs. MSCs can be isolated from virtually every tissue and organ including, but not limited to, bone marrow, pancreas, heart, adipose tissue, lung, liver, skin, kidney, and thyroid gland. MSCs can also be produced from pluripotent cells, such as embryonic stem cells and induced pluripotent cells. Trivedi and Hematti, Exp. Hematol. 36(3):350-359 (2008).

Figure 1:
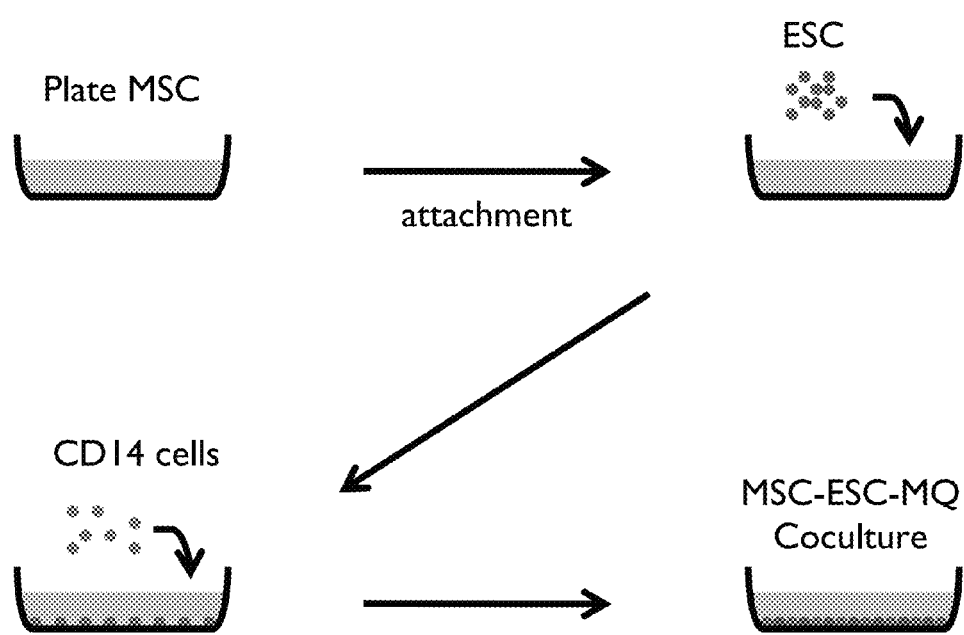
FIG. 1 illustrates one embodiment of a possible co-culture protocol for developing tissue-specific progenitor cells.
Figure 3A:
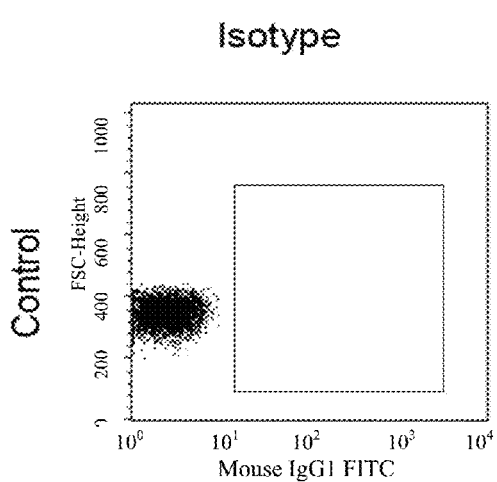
FIG. 3A-D illustrate animal engraftment of CD34$^+$ cells produced by the described co-culture protocol. Peripheral blood cells from control (FIG. 3A, FIG. 3B) or engrafted (FIG. 3C, FIG. 3D) sheep were analyzed by flow cytometry using isotype control antibodies (FIG. 3A, FIG. 3C) or anti-CD45 antibody (FIG. 3B, FIG. 3D).
Figure 3B:
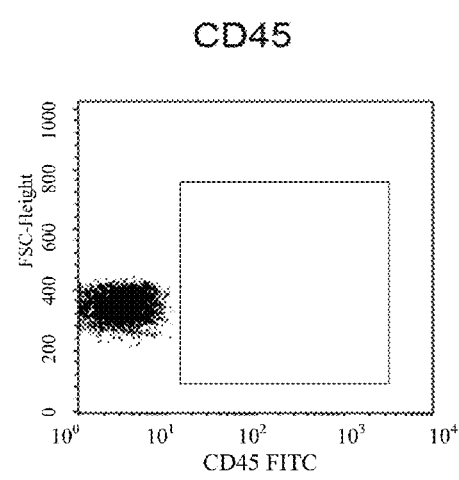
Figure 3C:
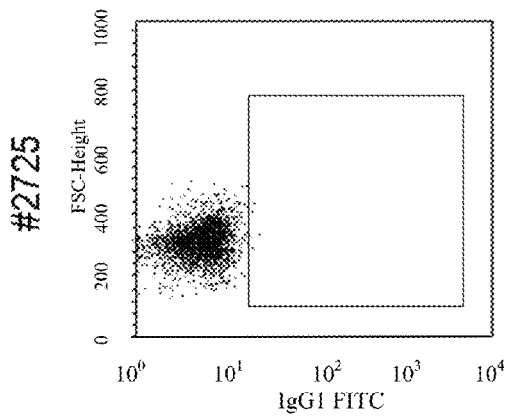
Figure 3D:
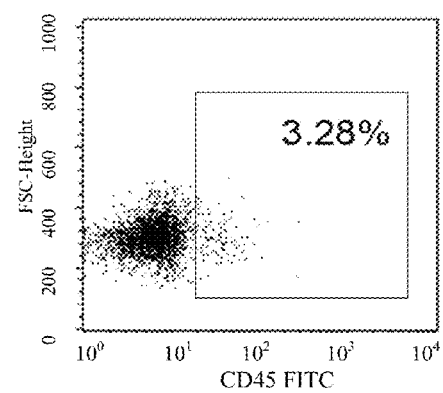

FIG. 1 illustrates one possible co-culture protocol. According to the illustrated embodiment, MSCs derived from a desired tissue are plated into a culture dish and allowed to adhere, e.g., for approximately 24 hours. MSCs attach well to plastic surfaces but can be grown on any suitable surface (e.g., glass, ceramic, polymers) or matrix (e.g., collagen, laminin, MATRIGEL™). Pluripotent cells, such as embryonic stem cells or induced pluripotent stem cells, can then be added to the MSC layer and, optionally, cultured for expansion. Alternatively, MSCs and pluripotent stem cells can be added together. CD14$^+$ cells are then added to the MSC-pluripotent cell culture. In some embodiments, all three cell types are added to the culture together. In some embodiments, the pluripotent stem cells or macrophages are placed in culture first, followed by the addition of the remaining two cell types (together or in sequence). In some embodiments, alpha 20 medium (alpha-Modified Eagle Medium, 20% FBS) is used for culture. Other media can be used for one or more of the culture steps, such as R10 medium (RPMI1640 medium, 10% FBS), MSC medium (alpha-Modified Eagle Medium, 20% FBS), and C10 medium (CMRL1066 medium, 10% FBS). In some embodiments, more than one kind of medium can be used. For example, TeSR medium can be used for a MSC-pluripotent cell culture step, followed by a MSC-CD14$^+$ cell-pluripotent cell co-culture in alpha 20 medium.

The co-culture can be maintained under normoxic (21% oxygen) or hypoxic (5% oxygen) culture conditions. Incubation time required for tissue specific progenitor cell generation can vary depending on the culture objective. Fresh media are typically provided every two to three days, for example, by removing half of the spent media and adding fresh media to the culture to restore the desired culture volume. In some embodiments, monothioglycerol is added to the culture (e.g., at 300 µM) to prevent oxidative damage. Co-cultures can subsequently be tested for the presence of progenitor cells by assessing, for example, cell morphology or cell marker expression.

MSCs, CD14+ cells, and pluripotent cells can be autologous, syngeneic, or allogeneic with respect to each other. The skilled artisan will appreciate the advantageous efficiency of generating progenitor cells from pluripotent cells that were derived from the patient who is to receive the progenitor cells. For example, somatic cells, such as skin cells could be reprogrammed to pluripotent cells. These cells are genetically identical to the patient and, as such, the resulting progenitor cells produced by Applicants' methods are also genetically identical to the patient, reducing the risk of adverse reaction after administration.

Monocytes isolated from peripheral blood can be cultured for various times and under various conditions before addition to the MSC-ESC culture or can be added directly. The skilled artisan will appreciate that monocytes/macrophages, pluripotent cells, and MSCs employed in methods described herein can be cultured in any medium that supports their survival and growth. Further, co-cultures do not require the addition of cytokines, although cytokines or growth factors can be added.

Monocytes or macrophages can be co-cultured with MSCs and pluripotent cells such that the cells are in direct physical contact. Alternatively, the monocytes or macrophages can be placed in a subcompartment separate from the subcompartment containing the MSCs and pluripotent cells, such that the subcompartments are in fluid communication but separated by a semi-permeable membrane. The semi-permeable membrane allows the exchange of soluble media components and factors secreted by the cells but is impenetrable to the cells themselves. The pores within the semi-permeable membrane typically are between 0.1-1.0 µm, but other pore sizes can be suitable.

The co-cultured cells can be allogeneic, syngeneic, or autologous with respect to each other. As used herein, "allogeneic" refers to cells or tissues taken from different individuals of the same species that are not genetically identical. As used herein, "syngeneic" refers to cells or tissues that are genetically identical or closely related. As used herein, "autologous" refers to cells or tissues taken from the same individual that are genetically identical.

The resulting tissue-specific progenitor cells described herein are readily distinguished from undifferentiated pluripotent cells in that they assume different morphology and/or express a unique set of markers. For example, HSCs differ from undifferentiated cells in that they express CD34. HSCs are medium sized with large nuclei eccentrically surrounded by narrow rims of cytoplasm that appears deep blue after Grunwald-Giemsa staining and occasionally contains cytoplasmic granules (Stella et al., Haematologica 80(4):367 (1995)).

Various methods of cell separation are known in the art and can be used to separate the resulting tissue-specific progenitor cells from the MSCs, macrophages, and undifferentiated cells depending on factors such as the desired purity of the isolated cell populations. Tissue-specific progenitor cells can be maintained in culture in any medium that supports their in vitro growth and survival. Also, tissue-specific progenitor cells can be stored using methods known in the art including, but not limited to, refrigeration, cryopreservation, vitrification, and immortalization.

It is contemplated that the tissue-specific progenitor cells can be administered to an individual for treating conditions associated with aberrant tissue maintenance, repair, or function. Conditions associated with aberrant tissue maintenance, repair, or function include, but are not limited to, myocardial infarction, diabetes, aplastic anemia, heart failure, cirrhosis, and liver failure. Specifically contemplated herein are methods for supporting and/or restoring hematopoiesis in an individual in need thereof, comprising administering an HSC produced by the described methods to an individual in need thereof. The ESC-derived HSCs can also be used to generate progenies of HSCs in vitro, such as RBC and platelets, for transfusion purposes.

It is specifically contemplated that HSC produced by the described methods can be administered to an individual to induce tolerance to cells and cell products that originate from the same source as the engrafted cells. For example, beta islet cells produced from an ESC line will be tolerated by individuals that previously received HSC produced from the same ESC line.

It is specifically contemplated that one can provide sufficient autologous tissue-specific progenitors for clinical application by co-culturing autologous monocytes or macrophages with allogeneic MSCs and pluripotent cells from a universal source. Tissue-specific progenitors administered to an individual can be autologous, syngeneic, or allogeneic with respect to the individual. One of skill in the art will appreciate the advantageous efficiency of using an autologous progenitor, i.e., the administered progenitor was derived from a pluripotent cell that was taken from the same individual as the recipient.

Another application for tissue-specific progenitors contemplated by the inventors is an in vitro screening method for compounds that modulate progenitor cells and their developmental or differentiation processes. For example, to determine how a compound affects hematopoiesis, hematopoietic progenitors, such as HSCs, can be produced by applicants' method and cultured in the presence of the compound of interest. As used herein, "modulate" means promote, enhance, inhibit, or in any other way alter normal cell function.

The progenitors can be administered to an individual through any suitable delivery method. A delivery method can include topical application, such as application to a wound. For example, progenitors can be delivered in a pharmaceutically acceptable carrier or dressing, examples of which include a liquid, oil, lotion, salve, cream, foam, gel, paste, film, or hydrogel. Parenteau, Regen. Med. 4(4):601-611 (2009). Exemplary carriers and dressings having suitable properties are well-known by those of ordinary skill in the art. The choice of a specific carrier is influenced by factors such as nature of the condition, number of cells to be administered, route of administration, and duration of treatment. Urbaniak Hunter et al., Adv. Exp. Med. Biol. 671: 117-130 (2010). Progenitors can also be delivered through local or systemic injection, by surgical transplantation or implantation, or by other methods known in the art. Progenitors can be autologous, syngeneic, or allogeneic with respect to the receiving individual and with respect to MSCs and macrophages used for their generation.

The term "tissue-specific MSC" as used herein, means an MSC isolated from a single tissue or organ of an individual.

As used herein, "tissue-specific progenitor cell" means a progenitor cell committed to a specific tissue lineage.

Another application for MSC-macrophage cocultures contemplated by the inventors is ex vivo expansion of cells isolated from an individual. These cells can include undifferentiated cells, such as multipotent and pluripotent stem cells, or abnormal cells, such as malignant cells.

The invention will be more fully understood upon consideration of the following non-limiting Examples.

EXAMPLES

Example 1

Isolation of Human Monocytes and Mesenchymal Stem Cells

All protocols were approved by the Health Sciences Institutional Review Board of University of Wisconsin-Madison School of Medicine and Public Health.

Monocytes were derived from peripheral blood of human volunteers. Monocytes were isolated from human peripheral blood using magnetic bead separation according to manufacturers' instructions, briefly described as follows. Peripheral blood mononuclear cells were isolated from the blood of healthy volunteers by density gradient separation using Percoll (GE Healthcare Bio-sciences, Piscataway, N.J., USA). Contaminating red blood cells were lysed by incubating the mononuclear cells in ACK lysis buffer for 3 minutes, followed by a wash in phosphate buffered saline (PBS). To reduce platelet contamination, the cells were centrifuged at 700 rpm for 15 minutes. The resulting cell pellets were resuspended and incubated with MicroBeads conjugated to anti-human CD14 antibodies (Miltenyi Biotech, Auburn, Calif., USA) for 15 minutes at 4° C. The cells were washed to remove unbound antibody, and separated using autoMACS Pro Separator (Miltenyi Biotech). Ninety-five percent of the purified cells expressed CD14, as determined by flow cytometry. Purified $CD14^+$ monocytes were plated into the wells of 6-well cell culture plates at a concentration of $0.5-1\times10^6$ cells per well in Iscove's Modified Dulbecco's Medium (IMDM) supplemented with 10% human serum blood type AB (Mediatech, Herndon, Va., USA), 1× non-essential amino acids (NEAA-Lonza, Walkersville, Md., USA), 4 mM L-Glutamine (Invitrogen, Carlsbad, Calif., USA), 1 mM Sodium pyruvate (Mediatech), and 4 ug/ml recombinant human insulin (Invitrogen). To generate macrophages, $CD14^+$ monocytes were cultured at 37° C. with 5% $CO_2$ for approximately 3-7 days, without adding any cytokines, changing the media once 3-4 days after initiating the cultures.

MSCs were isolated from filters left over from standard filtration of bone marrow harvests from healthy donors. Briefly, the bone marrow cells trapped in the filter were collected by washing the filter with PBS. Mononuclear cells were separated using Ficoll-Hypaque 1.073 (GE Healthcare Bio-sciences) and Leucosep tube (Greiner Bio-one, Monroe, N.C., USA) according to the manufacturer's instructions. Contaminating red blood cells were lysed by incubating the mononuclear cells in ACK lysis buffer for 3 minutes. Mononuclear cells were suspended in alpha minimum essential medium (αMEM) supplemented with 10% fetal bovine serum (FBS, Hyclone, Logan, Utah, USA), 1×NEAA, and 4 mM L-Glutamine. Cells that attached to the culture dish (passage 0) were harvested using TrypLE cell dissociation enzyme (Invitrogen) and then replated into new flasks, as described by Trivedi and Hematti, Exp. Hematol. 36:350-359 (2008), incorporated herein by reference as if set forth in its entirety. Passage 4 cells were characterized by flow cytometry and by multi-differentiation assays for MSC characteristics (Dominici et al., Cytotherapy 8(4):315 (2006)).

Example 2

Bone Marrow-Derived MSCs and Macrophages Stimulate Differentiation of hES Cells into $CD34^+$ Cells In Vitro Cells Monocytes and MSCs were isolated essentially as described in Example 1. The Embryonic stem cell (ESC) line WA01 was supplied from WiCell Institute. ESCs were maintained on Matriger™-coated plates (BD Biosciences, San Jose, Calif.) in TeSR media (WiCell, Madison, Wis.) according to standard protocol published by WiCell Institute (Ludwig et al. Nat. Methods 3(8):637-646 (2006), incorporated herein by reference as if set forth in its entirety). Briefly, ESCs cultured on Matrigel™ were treated with 1 mg/ml dispase (Invitrogen, Carlsbad, Calif.) for 7 minutes (5 minutes for xeno-free matrix cultured ESC). Cells were washed with DMEM/F12 three times and were collected by scraping with a glass pipette. The harvested cells were gently pipetted to dissociate large colonies and were added to Matrigel™-coated plates for expansion.

MSC-ESC Co-Culture

MSCs were plated into 6-well plates at a density of $1\times10^5-3\times10^5$ cells per well in media. The media used at this stage were determined by the target tissue in question but any medium containing FBS was determined to be suitable for preparing MSC feeder layers for ESCs. For bone marrow MSC plating, R10 medium was used, which contains RPMI1640 medium (Mediatech, Manassas, Va.) supplemented with 10% FBS (Atlanta Biologicals, Lawrenceville, Ga.), 1% non-essential amino acid, 1% L-Alanine-L-Glutamine and 1% Sodium pyruvate (Mediatech, Manassas, Va.). After 1 hour, plates were ready for use as ESC feeder. ESCs were harvested using dispase treatment as described above. ESCs were maintained on MSC feeders for several days in TeSR media to allow for ESC expansion and colony formation (about 3-4 days).

MSC-ESC-$CD14^+$ Cell Co-Culture $CD14^-$ cells were added to ESC-MSC co-cultures at a concentration of about $1\times10^6$ cells per well. The $CD14^+$ cells used for these experiments were either monocytes from peripheral blood that were fresh or stored frozen, or macrophages derived from $CD14^+$ monocytes by culturing monocytes for more than 1 week in vitro. The ESC-MSC-$CD14^+$ cell co-cultures were incubated in R10 medium, which was changed every three to four days by collecting floating cells in the supernatant through centrifugation and resuspending them in fresh medium which was then added back to the original culture plates.

Several media and media combinations were used for MSC-ESC- and MSC-ESC-$CD14^+$ cell co-culture, such as alpha 20 medium (alpha-Modified Eagle Medium, 20% FBS) R10 medium (RPMI1640 medium, 10% FBS), MSC medium (alpha-Modified Eagle Medium, 20% FBS), and C10 medium (CMRL1066 medium, 10% FBS). Other media that can support progenitors of a desired linage can be used with the described culture methods. Also, MSCs, pluripotent cells, and $CD14^+$ cells were added to the co-culture together or in various sequence. MSCs or $CD14^+$ cells each adhered readily to untreated culture dishes and supported subsequent pluripotent cell adhesion.

To determine the effect of low oxygen on the generation of tissue specific progenitor cells, some of the culture experiments were conducted under hypoxic conditions. Oxygen levels were reduced to 5% within cell culture incubators by using the nitrogen purge method, essentially as described by Simon et al, Nat. Rev. Mol. Cell Biol. 9(4):285 (2008), incorporated herein by reference as if set forth in its entirety.

ESC-MSC-Macrophage Co-Culture Analysis using Flow Cytometry

For flow cytometric analysis, cells were collected by aspirating medium, washing with PBS once and then treating with TrypLE enzyme for 5 minutes. After neutralization of TrypLE enzyme by adding equal volume of medium, cells were stained for flow cytometry. Briefly, cells were centrifuged to remove culture medium and incubated with antibody for 30 minutes at 4° C. Cells were then washed with wash buffer (PBS with 0.5% human serum albumin, 2 mM EDTA and 0.05% sodium azide) before use for analysis. To assess hematopoietic cell generation, anti-CD38 PE, anti-CD41 FITC, anti-CD43 PE, anti-CD73 PE, and anti-hematopoietic progenitor cell antibody PE (BD biosciences, San Jose, Calif.) were used. Anti-CD14 FITC, anti-CD26 PE, anti-CD45 PE, anti-CD235a FITC (eBioscience, San Diego, Calif.), and anti-CD133 PE (Miltenyi Biotec, Auburn, Calif.) antibodies were also used for analysis.

Cell Isolation for Tissue Progenitor Cell Enrichment

Cells from ESC-MSC-Monocyte/Macrophage co-culture were sorted using magnetic bead-based separation to enrich tissue progenitor cells. For CD34$^+$ cell isolation, trypsinized cells were sorted by CD34 microbead (Miltenyi Biotec, Auburn, Calif.) in the presence of Fc receptor blocker (Miltenyi Biotec, Auburn, Calif.) to block non-specific interaction.

Real Time PCR Analysis

RNA from progenitor cells enriched by magnetic bead separation was isolated with RNeasy mini kit (Qiagen, Valencia, Calif.) according to manufacturer's instructions. RNA quality and concentration was assessed using a Nano-Drop spectrophotometer (Thermo Scientific, Waltham, Mass.). RNA was converted to cDNA using Quantitect Sensiscript kit (Qiagen, Valencia, Calif.). Power SYBR green master mix (Applied Biosystems) was used for setting up RT-PCR plates according to the manufacturer's protocol. RT-PCR was performed using primers for GATA1, GATA2, GATA3, Flk1, Flt3, SCIL, and CD34 (Qiagen, Valencia, Calif.). Primers for 18S rRNA, GAPDH, and b-Actin (QIAGEN, Valencia, Calif.) were used as housekeeping gene controls. StepOnePlus system (Applied Biosystems) was used for detection.

Results

ESC-MSC-macrophage co-cultures generated CD34$^+$ hematopoietic cells when the MSCs were derived from bone marrow (FIG. 2A). When MSCs were derived from non-bone marrow sources, such as pancreas, co-cultures produced few if any CD34$^+$ cells (FIG. 2B). Co-cultures without MSCs or without macrophages (FIG. 2C) failed to produce CD34$^+$ cells, while small numbers of CD34$^+$ cells were produced in the absence of CD14$^+$ cells.

Figure 4:
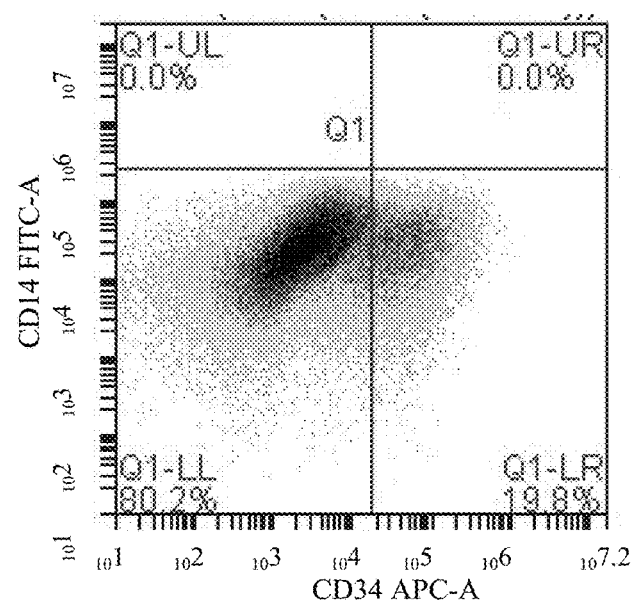
FIG. 4 illustrates an example of CD34$^+$ cell yield after bone marrow MSCs were co-cultured with ESCs and macrophages. The population was gated to exclude macrophages and apoptotic cells.
Figure 9:
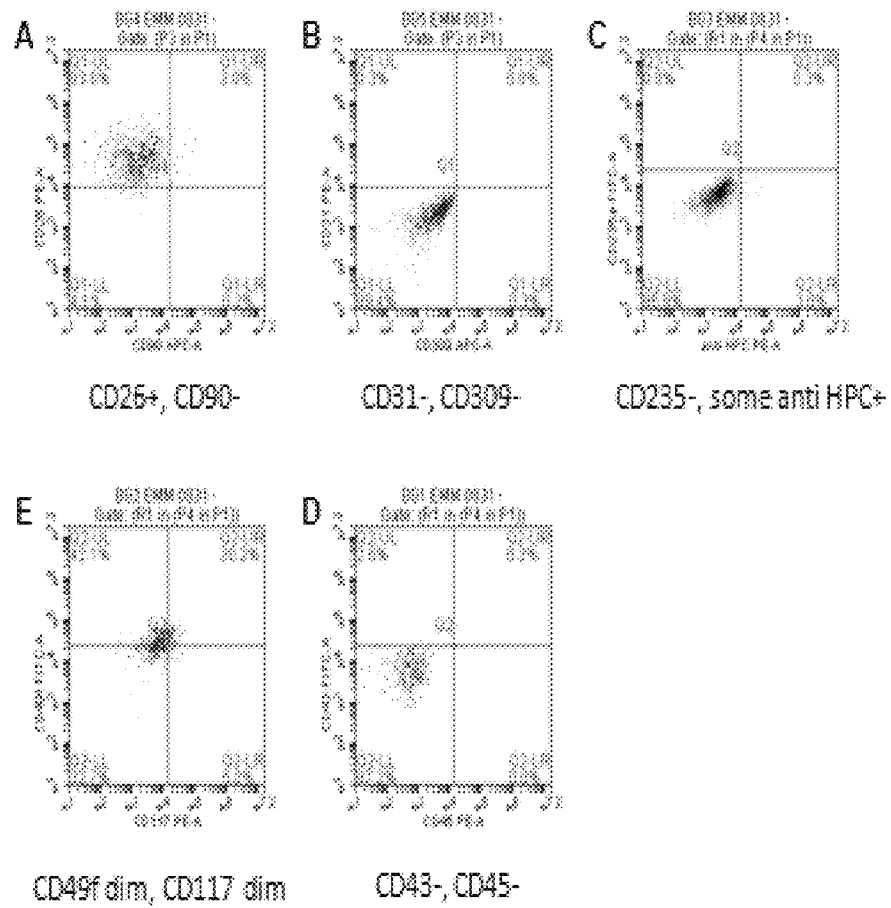
FIG. 9A-E illustrate flow cytometric analysis of CD34$^+$ cells produced by co-culture of bone marrow MSCs with ESCs and macrophages.

Flow cytometry using anti-CD14 antibodies confirmed that the CD34$^+$ staining was not due to non-specific antibody binding to Fc receptors. Co-staining with anti-CD73 antibodies confirmed that the CD34$^+$ cells do not express CD73, a marker for MSCs. CD34$^+$ cells also did not express CD13, CD14, CD31, CD38, CD41, CD43, CD45, CD73, CD90, CD235a, and CD309 (FIG. 9), suggesting that the cells are not endothelial cells, as indicated by the lack of CD31 expression, and are still uncommitted to specific lineages. Some CD34$^+$ cells generated in co-cultures expressed CD26 or anti-HPC antibody. The purity of the CD34$^+$ cell population was between 1 to 10%. Approximately 200,000 CD34$^+$ cells could be generated per well of a 6-well plate, a yield adequate to produce numbers of CD34$^+$ cells sufficient for clinical applications. Up to 20% of non-macrophage-, non-apoptotic cells expressed CD 34 after co-culture (FIG. 4). Hypoxia increased the yield of CD34$^+$ cells after co-culture.

To confirm that the CD34$^+$ cells were hematopoietic cells, CD34$^+$ cells were isolated using magnetic beads. Real time PCR on RNA from the isolated CD34$^+$ cells revealed that these cells express GATA2, GATA3, Flk1, Flt3, and CD34. The CD34$^+$ cells also expressed FOXA2. While co-cultures with non-bone marrow derived MSCs (e.g., pancreas MSCs) produced very few CD34$^+$ cells, the few CD34$^+$ cells derived from those cultures had several fold lower expression of MSC, GATA3, Flt3, and CD34.

To rule out the possibility that the results of the real time PCR analysis were due to contaminating MSCs, real time PCR was performed on bone marrow MSC and pancreatic MSC. The result shows that although bone marrow MSCs express some of these genes, the level of expression for GATA3, FLT3, and CD34 was significantly lower compared to that of the CD34$^+$ cells isolated from bone marrow-derived MSC co-cultures.

Example 3

Tissue-Specific Progenitor Cell Engraftment In Vivo

Cells

Cells were isolated and co-cultured essentially as described in Examples 1 and 2. CD34$^+$ cells were isolated from ESC-MSC-Monocyte/Macrophage co-cultures using magnetic bead-based separation to enrich tissue progenitor cells.

Engraftment

To determine if the CD34$^+$ cells isolated from MSC-pluripotent cell-CD14$^+$ cell co-cultures can be engrafted and, subsequently, reconstitute a hematopoietic system, the pre-immune fetal sheep model was used. The fetal sheep model can be used to analyze multi-organ engraftment of human cells that are introduced in-utero prior to the development of the fetal immune system. Successful engraftment within the resulting human/sheep hematopoietic chimeras can be analyzed after birth. The engraftment was conducted essentially as described by Narayan et al., Blood 107:2180 (2005), incorporated herein by reference as if set forth in its entirety. On gestation day 61, three animals were engrafted with 0.5×10$^6$ CD34$^+$ cells each. The cells were delivered intra utero in serum-free media in a volume of 0.5 mL per fetus. After birth (gestation day 145-150), peripheral blood samples from engrafted and control lambs were analyzed using flow cytometry for the presence of human CD45$^+$ cells. The cells successfully engrafted and gave rise to 0.5-3.28% human CD45$^+$ cells in sheep peripheral blood (FIG. 3). This is a significant increase over previous attempts of human cell engraftment that resulted in only 0.1-0.2% engraftment (Narayan et al.). These results indicate that the methods described herein can be used to produce cells with superior ability to engraft into a recipient. As such, the methods described herein produce HSCs capable of long-term engraftment.

Example 4

Pancreatic Islet-Derived MSCs and Macrophages Stimulate Differentiation of hES Cells into Pancreas Cells In Vitro Cells Monocytes were isolated essentially as described in Example 1. The ESC line WA01 was supplied from WiCell Institute and maintained on Matriger™ essentially as described in Example 2. Pancreatic islet MSCs were derived from pancreatic islets collected from cadaveric donors per integrated islet distribution program protocol (IIDP) (available at the Diabetes Research Centers). Pancreatic islets were processed and yielded 10,000 to 20,000 islet equivalents. Islet cells were cultured in human MSC culture medium for several days until they attached to the culture flasks. Human MSC culture medium contained aMEM medium supplemented with 10% FBS. In some cases, non-essential amino acids and L-Glutamine was also added to the medium. Cells were harvested with TrypLE and passaged up to passage 4. Islet-derived MSCs were characterized by flow cytometry as described in Example 1 and were tested for differentiation potential. Briefly, pancreatic islet-derived MSCs were cultured in nonhematopoietic stem cell differentiation medium (Miltenyi Biotec, Auburn, Calif.) for differentiation into adipose, chondrogenic, and osteogenic tissue according to the manufacturer's protocol. The cells differentiated into cells of all three lineages, demonstrating that the cells were MSCs.

MSC-ESC Co-Culture

MSCs were plated into 6-well plates at a density of $1 \times 10^5$-$3 \times 10^5$ cells per well essentially as described in Example 2 except that for pancreatic islet-derived MSCs, C10 medium was used which was made by supplementing CMRL1066 medium (Mediatech, Manassas, Va.) with 10% FBS (Atlanta Biologicals, Lawrenceville, Ga.), 1% NEAA, and 1% L-Alanine-L-Glutamine (Mediatech, Manassas, Va.).

MSC-ESC-CD14$^+$ Cell Co-Culture

CD14$^+$ cells were added to ESC-MSC co-cultures at a concentration of about $1 \times 10^6$ cells per well essentially as described in Example 2. The ESC-MSC-CD14$^+$ cell co-cultures were incubated in C10 media, which was changed every three to four days by collecting floating cells in the supernatant through centrifugation and resuspension in fresh medium which was then added back to the original culture plates.

ESC-MSC-Macrophage Co-Culture Analysis using Flow Cytometry

For flow cytometric analysis, cells were collected, washed, and stained essentially as described in Example 2 except that CD14 FITC (eBioscience, San Diego), CD73 PE (BD Biosciences, San Jose, Calif.), HPi2, HPx2, HPd1, and HPa1 (Stemgent, Cambridge, Mass.) antibodies were used. These antibodies recognize pancreas-specific cell markers that can be used to enrich specific pancreas lineage cells. Dorrell, Stem Cell Res. 1(3):183-194 (2008). Goat anti-mouse FITC secondary antibody or zenon Alexa 488 mouse IgG1 kit were used for signal detection.

Cell Isolation for Tissue Progenitor Cell Enrichment

Cells from ESC-MSC-CD14$^+$ cell co-cultures were sorted using magnetic bead-based separation to enrich tissue progenitor cells. Harvested cells were depleted of macrophages using CD14 microbeads. Negative fractions from CD14 isolation were incubated with HPi2 antibody for 15 minutes at 4° C. and then washed with autoMACS running buffer. Cells were then incubated for 15 minutes with anti-mouse IgG microbeads (Miltenyi Biotec, Auburn, Calif.) and subsequently positively selected by autoMACS pro system. Both HPi2 positive and negative fractions were kept for comparison purposes.

Real Time PCR Analysis

RNA from progenitor cells enriched by magnetic bead separation was isolated and subjected to real time PCR analysis essentially as described in Example 2. RT-PCR was performed using primers for FOXA2, Insulin, Glucagon, PDX1, SLC2A2, G6PC2, and SOX7 (Qiagen, Valencia, Calif.). Primers for 18S rRNA, GAPDH, b-Actin (QIAGEN, Valencia, Calif.) were used as housekeeping gene controls. StepOnePlus system (Applied Biosystems) was used for detection.

Results

ESC-MSC-macrophage co-cultures generated pancreatic islet progenitor cells when the MSCs were derived from pancreatic islets. Several monoclonal antibodies known to enrich certain populations of pancreatic cells were used to detect pancreatic islet progenitor cells. HPi2 antibody which is known to enrich islet cells stained the resulting progenitors. When the MSCs used for co-culture were derived from bone marrow, few cells stained with HPi2 antibody. The pancreatic islet cells generated in co-culture did not stain with HPx2 (exocrine cells), HPa1 (pancreatic alpha cell), or HPd1 (pancreatic duct) antibodies. These cells also did not express CD14 and CD73, confirming that these cells were neither macrophages nor mesenchymal cells.

Example 5

In Vitro Progenitor Development Testing Platform

Figure 5:
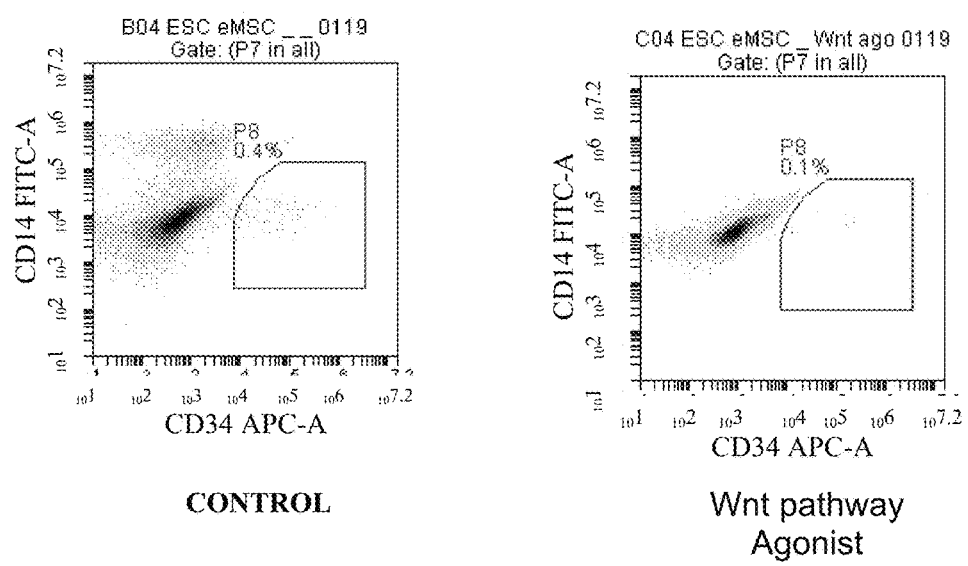
FIG. 5 illustrates an example of in vitro screening for compounds that modulate tissue-specific progenitor cell development. Bone marrow MSCs were co-cultured with ESCs and macrophages in the presence (Wnt pathway agonist) or absence (control) of the Wnt pathway agonist 2-Amino-4-(3,4-(methylenedioxy)benzylamino)-6-(3-methoxyphenyl)pyrimidine and analyzed by flow cytometry.

The co-culture system described in Example 2 was used as an in vitro testing platform to determine the potential effect of agents on tissue/organ development. Cells for ESC-MSC-CD14$^+$ cell co-cultures were prepared essentially as described in Example 1. A non-specific Wnt pathway agonist (cat. No. 681665-5 mg, EMD Millipore, USA) was tested for its effect on CD34$^+$ cell generation as Wnt1 activation is known to play role in hematopoiesis during embryonic development. Significantly fewer CD34$^+$ cells were present in co-cultures in the presence of the Wnt pathway agonist, compared to co-cultures without the agonist (FIG. 5). This result suggests that the Wnt pathway agonist might interfere with hematopoiesis.

Example 6

MSCs-Macrophages Co-Culture Stimulates Proliferation of CD34$^+$ Cells In Vitro

MSCs were harvested from healthy BM and passaged as described in Example 1. Macrophages were derived as described in Example 1. MSCs-macrophage co-culture experiments were conducted as described in Example 2. Human G-CSF mobilized CD34$^+$ cells were stained with 10 µM carboxyfluorescein diacetate succinimidyl ester (CFSE) for 15 minutes at 37° C., washed, and seeded into 6-well plates with a) no supportive cells, b) MSCs, c) macrophages, or d) MSCs and macrophages. CFSE is a dye that penetrates cell membranes and becomes trapped inside cells after intra-cellular enzymatic cleavage. The amount of CFSE per cell decreases by half with each cell division. Cells were cultured for four days and subsequently analyzed by Fluorescence-activated cell sorting (FACS) and proliferation indices were calculated using ModFit software. The proliferation index (PI) is the sum of the cells in all generations divided by the calculated number of cells initially subjected to the assay. CD34$^+$ cells co-cultured with MSCs or macrophages showed higher levels of proliferation (PI=2.09 and PI=1.82, respectively) compared to CD34$^+$ cells cultured in the absence of these cells (PI=1.31). CD34$^+$ cells co-cultured with both MSCs and macrophages show the highest rate of proliferation (PI=2.80). This data suggest that MSC-macrophage interactions support CD34+ cell proliferation, a contribution of macrophages not previously investigated.

Example 7

In Vitro Expansion of Multiple Myeloma Cells

The MM cell lines U266 and NCI-H929 were acquired from American Type Culture Collection (ATCC) and were cultured according to recommended protocol. Briefly, U266 cells were cultured in RPMI 1640 with 10% FBS, 1% NEAA, 2 µM L-alanine-L-glutamine and 1% sodium pyruvate, and medium was changed every two to three days. U266 MINI cells were stained with 10 µM CF SE for 15 min at 37 C, washed twice in PBS containing 0.5% HSA, and added to 6-well plates at a concentration of 200,000 cells per well with a) no supportive cells, b) MSCs, c) macrophages, or d) MSCs and macrophages. Cells were cultured for four days and subsequently analyzed by flow cytometry. Proper gating was necessary as some macrophages were dimly positive for CFSE because they had phagocytosed CFSE-stained MM cells. Proliferation indices were calculated with ModFit software.

Figure 6:
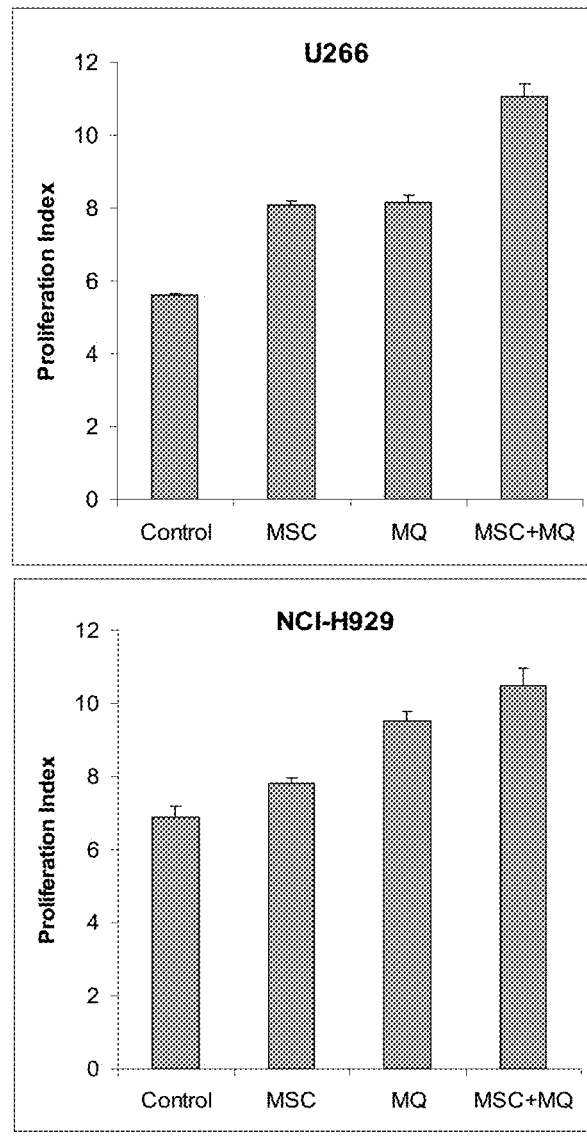
FIG. 6 illustrates proliferation indices of U266 and NCI-H929 MM cell lines.

FIG. 6 depicts the mean proliferation index (PI) calculated from three separate experiments, each performed in triplicate, using MSCs and macrophages (MQ) from separate healthy donors. MSCs enhanced U266 proliferation (PI=7.24) compared to U266 grown in the absence of supporting cells (PI=4.21). This is consistent with the long-held belief that MSCs act as a main stromal component for MM malignancy. Hideshima et al., Nat. Rev. Cancer 7:585-598 (2007). Interestingly, macrophages enhanced U266 proliferation (PI=11.84) beyond that observed with MSCs. The highest level of U266 proliferation could be observed in cultures containing both MSCs and macrophages (PI=12.92). Similar results were consistently observed in further experiments using both U266 or NCI-H292 MM cell lines. Similar results were also obtained when the experiments were conducted using RPMI1640 with 10% FBS and RPMI1640 with 0.5% human serum albumin, demonstrating that the observed increase in MM cell proliferation was not due to contaminating macrophage media (IMDM supplemented with 10% human serum AB). These results suggest that the macrophage-MSC interaction enhances tumor cell growth.

Example 8

Figure 7:
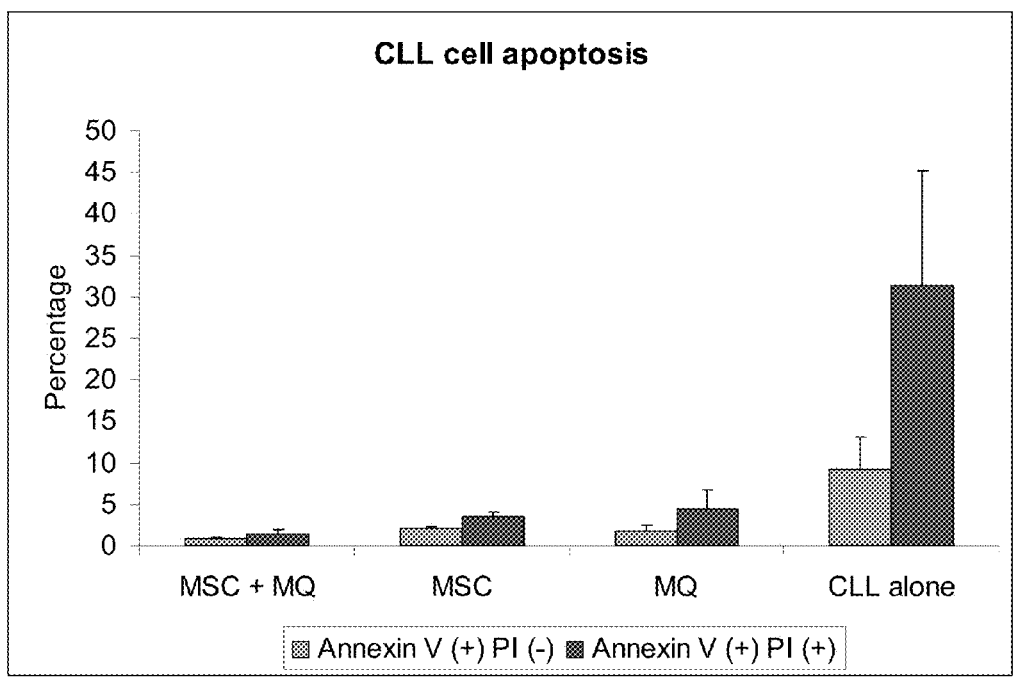
FIG. 7 illustrates the percent apoptotic chronic lymphocytic leukemia cells in culture either alone (CLL alone), in the presence of macrophages (MQ), MSCs (MSC), or macrophages and MSCs (MSC+MQ).

MSC-CD14+ Cell Co-Culture with Normal or Malignant Cells Reduces Apoptosis In Vitro In vitro maintenance of primary malignant cells is challenging in part because the cells undergo programmed cell death (apoptosis). To determine if co-culture with MSCs and CD14+ cells affects apoptosis of malignant cells in culture, primary chronic lymphocytic leukemia cells were cultured either alone (FIG. 7, CLL alone), with bone marrow MSCs (FIG. 7 MSC), with macrophages (FIG. 7, MQ), or with MSCs and macrophages (FIG. 7, MSC+MQ). The cells were analyzed for Annexin V binding to the cell surface, a marker for early stage apoptosis, and for propidium iodide staining, a marker for late stage apoptosis or necrosis. Early apoptotic cells are Annexin $V^+/PI^-$, late apoptotic cells are Annexin$^+$/PI$^+$.

Figure 8:
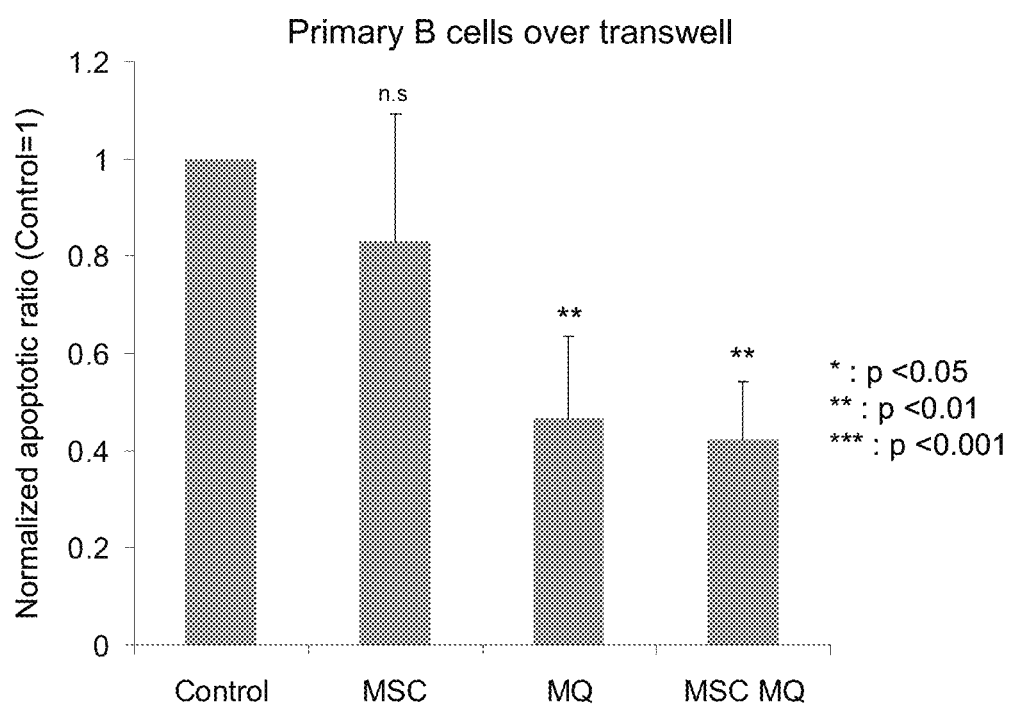
FIG. 8 illustrates normalized apoptotic ratios for primary B-cells cultured alone (control), or in the presence of macrophages (MQ), MSCs (MSC), or macrophages and MSCs (MSC MQ).

Primary CLL cells exhibited decreased apoptosis in the presence of either MSCs or macrophages (FIG. 7). The greatest decrease in apoptosis was observed when the primary CLL cells were co-cultured with both MSCs and macrophages (FIG. 7). Similar protection from apoptosis was observed for primary B cells cultured with either macrophages or MSCs and macrophages (FIG. 8), suggesting that the anti-apoptotic effect of MSC and macrophage co-culture is not limited to malignant cells.

We claim:

1. A cell culture composition comprising a CD14+ cell, a tissue-specific mesenchymal stem cell (MSC), and a pluripotent cell.

2. The cell culture composition of claim 1, wherein the CD14+ cell and the MSC are syngeneic with regard to each other.

3. A cell culture composition comprising a CD14+ cell, a tissue-specific mesenchymal stem cell (MSC), a pluripotent cell, and a tissue-specific progenitor cell.

4. The composition of claim 3, wherein the CD14+ cell is an MSC-educated macrophage.

5. The composition of claim 3, wherein the CD14+ cell is a monocyte.

6. The composition of claim 3, wherein the CD14+ cell and the MSC are syngeneic with respect to each other.

7. The composition of claim 3, wherein the CD14+ cell and the MSC are allogeneic with respect to each other.

8. The composition of claim 3, wherein the tissue specific MSC is selected from the group consisting of a cardiac-derived MSC, a pancreatic islet-derived MSC, and a bone marrow-derived MSC.

9. The composition of claim 3, wherein the tissue-specific progenitor is selected from the group consisting of a hematopoietic progenitor, a cardiomyocyte progenitor, and a pancreatic islet progenitor.

* * * * *

UNITED STATES PATENT AND TRADEMARK OFFICE
CERTIFICATE OF CORRECTION

PATENT NO. : 9,994,819 B2  
APPLICATION NO. : 15/154653  
DATED : June 12, 2018  
INVENTOR(S) : Peiman Hematti et al.

Page 1 of 1

It is certified that error appears in the above-identified patent and that said Letters Patent is hereby corrected as shown below:

In the Specification

Column 6, Line 3, "CD14-" should be --CD14$^+$--.

Column 7, Line 52, "Grunwald-Giemsa" should be --Grünwald-Giemsa--.

Column 9, Line 58, "1×NEAA" should be --1X NEAA--.

Column 10, Line 38, "CD14-" should be --CD14$^+$--.

Column 12, Line 67, "Matriger™" should be --Matrigel™--.

Column 13, Line 8, "aMEM" should be --αMEM--.

Column 15, Line 13, "MINI" should be --MM--.

Column 15, Line 13, "CF SE" should be --CFSE--.

Signed and Sealed this  
Sixteenth Day of October, 2018

Andrei Iancu  
*Director of the United States Patent and Trademark Office*